US00PP15549P2

(12) United States Plant Patent
Olesen et al.

(10) Patent No.: US PP15,549 P2
(45) Date of Patent: Feb. 8, 2005

(54) ROSE PLANT NAMED 'POULCS014'

(50) Latin Name: *Rosa hybrida*
Varietal Denomination: POULcs014

(75) Inventors: L. Pernille Olesen, Fredensborg (DK); Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 10/812,711

(22) Filed: Mar. 29, 2004

(51) Int. Cl.[7] ..... A01H 5/00
(52) U.S. Cl. ..... Plt./144
(58) Field of Search ..... Plt./144, 103

*Primary Examiner*—Anne Marie Grunberg
*Assistant Examiner*—June Hwu

(57) ABSTRACT

A new garden rose plant of the floribunda class which has abundant, creamy white flowers and attractive foliage. This new and distinct variety has shown to be uniform and stable in the resulting generations from asexual propagation.

2 Drawing Sheets

Botanical classification: *Rosa hybrida.*
Variety denomination: 'POULcs014'.

SUMMARY OF THE INVENTION

The present invention constitutes a new and distinct variety of garden rose plant of the floribunda class which originated from a controlled crossing between the female parent, an un-named seedling, and the male parent plant 'RUImired' Red Minimo, U.S. Pat. No. 5,770, dated Jul. 22, dated 1986. The two parents were crossed during the summer of 1991 and the resulting seeds were planted in a controlled environment in Fredensborg, Denmark. The new variety is named 'POULcs014'.

The new variety may be distinguished from its female seed parent, an un-named seedling, by the following characteristic: The seed parent has light pink flowers, while 'POULcs014' has white flowers.

The new variety may be distinguished from 'RUImired', the male pollen parent, by the following combination of characteristics:

1. While the pollen parent has red flowers, 'POULcs014' has white flowers.
2. While the pollen parent has 15 to 20 petals, 'POULcs014' has 50 to 55 petals.
3. While the pollen parent has no fragrance, 'POULcs014' has a moderate floral scent.

The objective of the hybridization of this rose variety was to create a new and distinct variety for garden use with unique qualities, such as:

1. Uniform and abundant white flowers;
2. Vigorous, but compact growth when propagated both as a budded rose and on its own roots;
3. Disease resistance.

This combination of qualities is not present in previously available commercial cultivars of this type, known to the inventors, and distinguish 'POULcs014' from all other varieties of which we are aware.

As part of their rose development program, L. Pernille Olesen and Mogens N. Olesen germinated the seeds from the aforementioned hybridization during winter of 1991 and conducted evaluations on the resulting seedlings in a controlled environment in Fredensborg, Denmark.

'POULcs014' was selected in the spring 1992 by the inventors as a single plant from the progeny of the aforementioned hybridization.

Asexual reproduction of 'POULcs014' by traditional budding and rooted cuttings was first done by L. Pernille and Mogens N. Olesen in their nursery in Fredensborg, Denmark in July, 1992. This initial and other subsequent asexual propagations conducted in controlled environments have demonstrated that the characteristics of 'POULcs014' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems, of 'POULcs014'. Specifically illustrated in the drawing: SHEET 1:

FIG. 1.1; Open flower, stem showing cluster of open flowers, branching, and the attachment of leaves, buds, and peduncles;

FIG. 1.2; Flower bud closed, flower bud as sepals unfold, and partially open;

FIG. 1.3; Flower petals, detached;

FIG. 1.4; Sepals, receptacle, and peduncle;

Specifically illustrated in SHEET 2:

FIG. 2.1; Juvenile stem with flower buds and leaves attached, exhibiting anthocyanin, FIG. 2.2; Juvenile leaves exhibiting anthocyanin;

FIG. 2.3; Mature leaf;

FIG. 2.4; Bare stem exhibiting thorns.

DETAILED DESCRIPTION OF THE VARIETY

The following is a description of 'POULcs014', as observed in its growth in a field nursery in Jackson County, Oreg. Observed plants are 3 years of age. Color references are made using The Royal Horticultural Society (London, England) Colour Chart, 1995, except where common terms of color are used.

For a comparison, several physical characteristics of the rose variety 'POULen001', a rose variety from the same inventors described and illustrated in U.S. Plant patent application Ser. No. 10/264,508 dated Oct. 4, 2002

(abandoned and a continuation of application No. 10/793,717 filed on Mar. 8, 2004), are compared to 'POULcs014' in Chart 1.

CHART 1

| | 'POULcs014' | 'POULen001' |
|---|---|---|
| Color of outer petals, inner surface upon opening | Green-White Group 157B | Yellow-White Group 158D |
| Petalage | 50 to 55 petals | 65 to 70 petals |
| Bloom Diameter | 63 mm | 65 to 70 mm |
| Color of basal petal spot, upon opening | Yellow Group 4C | Green-Yellow Group 1D |

FLOWER AND FLOWER BUD

Blooming habit: Continuous.

Flower bud:

*Size.*—Upon opening, 26 mm in length from base of receptacle to end of bud. 15 mm diameter on average.

*Bud form.*—Broad-based.

*Bud color.*—As sepals unfold, petals are Yellow-Green Group 145D with intonations of Red Group 53C. At ¼ opening petals are Yellow-Green Group 145D with intonations of Red Group 53C.

*Sepals.*—Upper Surface: Color: Yellow-Green Group 144A. Surface: Slightly pubescent. Lower Surface: Color: Yellow-Green Group 144A. Texture: Scant stipitate glands. Sepal Shape: Sepal apex is cirrhose. Base is flat at union with receptacle. Sepal Margin: Margins have weak foliaceous appendages on three of the five sepals. Size: 21 mm (l)×7 mm (w).

*Receptacle.*—Surface Texture: Smooth and glabrous. Shape: Funnel shaped. Size: 8 mm (h)×7 mm (w). Color: Yellow-Green Group 144A.

*Peduncle.*—Surface: Smooth. Length: 30 to 55 mm. Color: Yellow-Green Group 144B. Anthocyanic pigments the color of Greyed-Red Group 181C observed. Strength: Strong.

*Borne.*—In clusters of 15 flower buds per stem.

Flower bloom:

*Fragrance.*—Moderate floral scent.

*Duration.*—The blooms have a duration on the plant of approximately 10 to 14 days. After flowers have fully matured, petals fall cleanly away from plant.

*Size.*—Flower diameter is 63 mm when open. Flower depth is 28 mm on average.

*Form.*—General shape is a shallow cup. Shape of flower when viewed from the side: Upon opening, upper part: Flat. Upon opening, lower part: Concave. Open flower, upper part: Flattened Convex. Open flower, lower part: Concave.

Petalage: 50 to 55 petals with 11 petaloids.

Color:

Upon opening, petals:

*Outermost petals.*—Outer side: Green-White Group 157B. Inner Side: Green-White Group 157B.

*Innermost petals.*—Outer side: Green-White Group 157B. Inner Size: Green-White Group 157B.

Upon opening, basal petal spots:

*Outermost petals.*—No distinctive coloration.

*Innermost petals.*—Outer side: Yellow Group 4C. Inner Side: Yellow Group 4C.

After opening, petals:

*Outermost petals.*—Outer side: Green-White Group 157B. Inner Side: Green-White Group 157B.

*Innermost petals.*—Outer side: Green-White Group 157B. Inner Side: Green-White Group 157B.

After opening:

*Outermost petals.*—No distinctive coloration at the petal base observed.

*Innermost petals.*—Outer Side: Yellow Group 4C. Inner Side: Yellow Group 4C.

General tonality: On open flower Green-White Group 157B with intonations of Yellow Group 10C. No change in the general tonality at the end of the $10^{th}$ day.

Petals:

*Petal reflex.*—Somewhat reflexed.

*Margin.*—Entire and uniform. Medium undulations of margin observed.

*Shape.*—Apex: Round. Base: Acute.

*Size.*—28 mm (l)×25 mm (w).

*Texture.*—Smooth.

*Thickness.*—Average.

*Arrangement.*—Not Formal.

Petaloids:

*Quantity.*—10 to 15.

*Color.*—Green-White Group 157B.

*Size.*—13 mm (l) ×10 mm (w).

*Shape.*—Somewhat irregular. Acute at the base. Rounded apex.

Reproductive organs:

*Pistils.*—Length: 9 mm. Quantity: 53 (actual count).

*Pollen.*—None observed.

*Anthers.*—Size: 2 mm in length. Color: Yellow-Orange Group 15A. Quantity: 109 (actual count).

*Filaments.*—Color: Yellow Group 1B. Length: 6 mm.

*Stigmas.*—Superior relative to the length of the filaments and the height of the anthers. Color: Greyed-Yellow Group 160D.

*Styles.*—Color: Yellow-Green Group 150D.

*Hips.*—None Observed in the field nursery in Jackson County Oreg.

PLANT

Plant growth: Moderate, upright to bushy. When grown as a budded field grown plant on *Rosa multiflora* understock, the average height of the plant is 60 to 100 cm and the average width is 60 to 100 cm.

Stems:

*Color.*—Young wood: Yellow-Green Group 144A. Older wood: Yellow-Green Group 144A.

*Surface texture.*—Young wood: Smooth. Older wood: Smooth.

Thorns:

*Incidence.*—3 thorns per 10 cm of stem.

*Size.*—Average length: 10 mm.

*Color.*—Yellow-Green Group 146C.

*Shape.*—Concave.

Plant foliage: Normal number of leaflets on normal leaves in middle of the stem: 7 leaflets.

*Compound leaf size.*—120 mm in length by 80 mm wide.

*Color.*—Mature Foliage: Upper surface is: Green Group 137A. Lower surface is: Yellow-Green Group 147B. Juvenile foliage: Upper surface is: Green Group 137A. Lower surface is: Yellow-Green Group 147B. Anthocyanin: Location: Juvenile foliage. Color: Greyed-Purple Group 185A.

Plant leaves and leaflets:

*Stipules.*—Size: 25 mm in length. Quantity: 2 per compound leaf. Margins: Finely serrated with few stipitate glands. Color: Yellow-Green Group 146A.

*Petiole.*—Length: 30 mm. Above: Color: Yellow-Green Group 144B. Anthocyanin: Greyed-Red Group 181B. Underneath: Observations: Thorns observed.

*Rachis.*—Size: 60 mm. Above: Color: Yellow-Green Group 144B. Underneath: Observations: Thorns observed.

*Leaflet.*—Size: 40 mm (l)×35 mm (w). Edge: Serrated. Texture: Smooth. Shape: Generally ovate. Apex is mucronate. Base is rounded. Thickness: Thick. Arrangement: Odd pinnate. Venation: Reticulate. Glossiness: Moderate glossy.

Disease resistance: Above average resistance to mildew, rust, black spot, and Botrytis under normal growing conditions in Jackson County, Oreg.

Cold hardiness: The variety 'POULcs014' has been found to be cold tolerant to USDA Cold Hardiness Zone 6.

It is claimed:

1. A new and distinct variety of rose plant named 'POULcs014' of the floribunda rose class, substantially as herein illustrated and described as a distinct and novel rose variety due to its abundant creamy white flowers, disease resistance, and extended period of bloom.

* * * * *

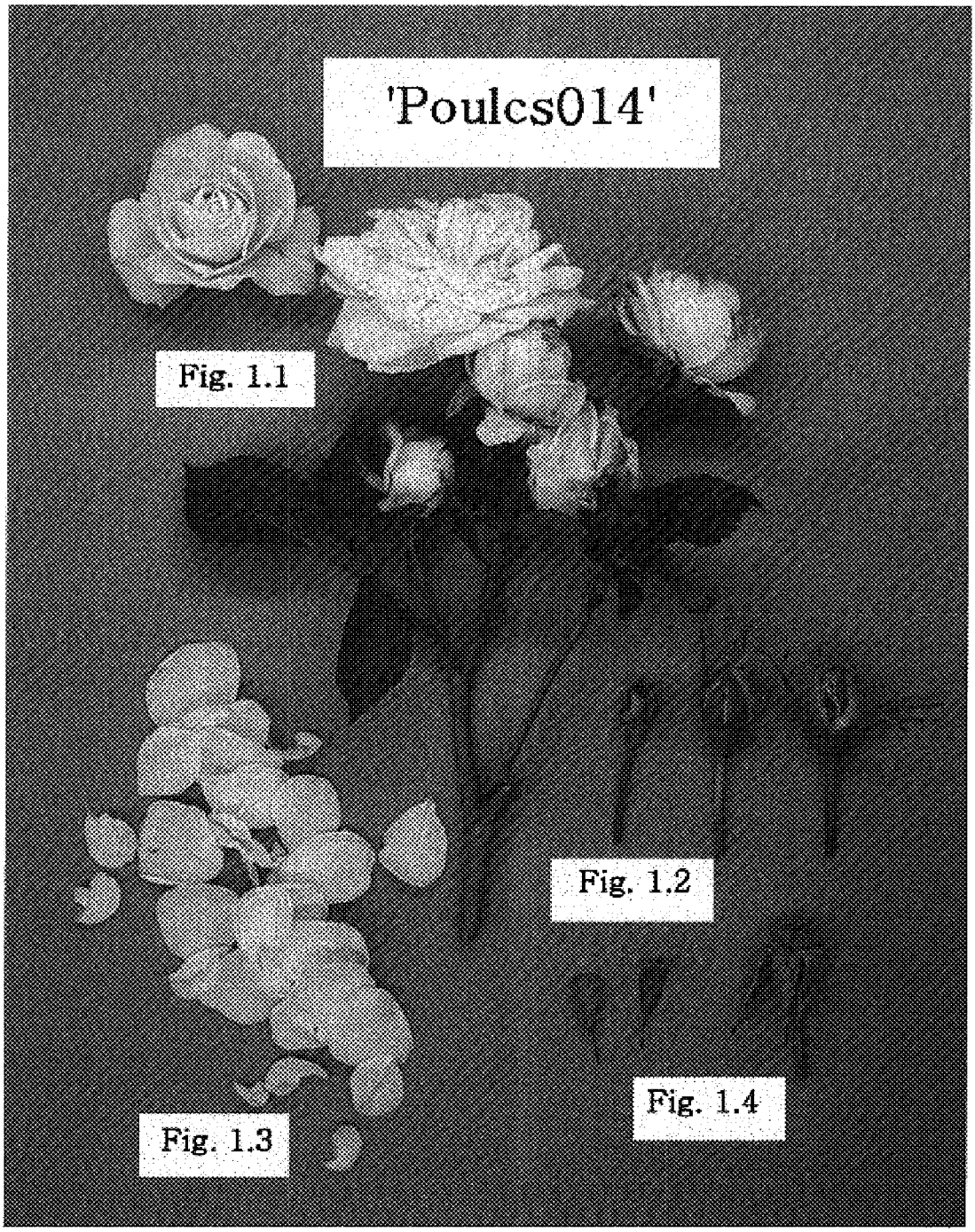
'Poulcs014'
Fig. 1.1
Fig. 1.2
Fig. 1.3
Fig. 1.4

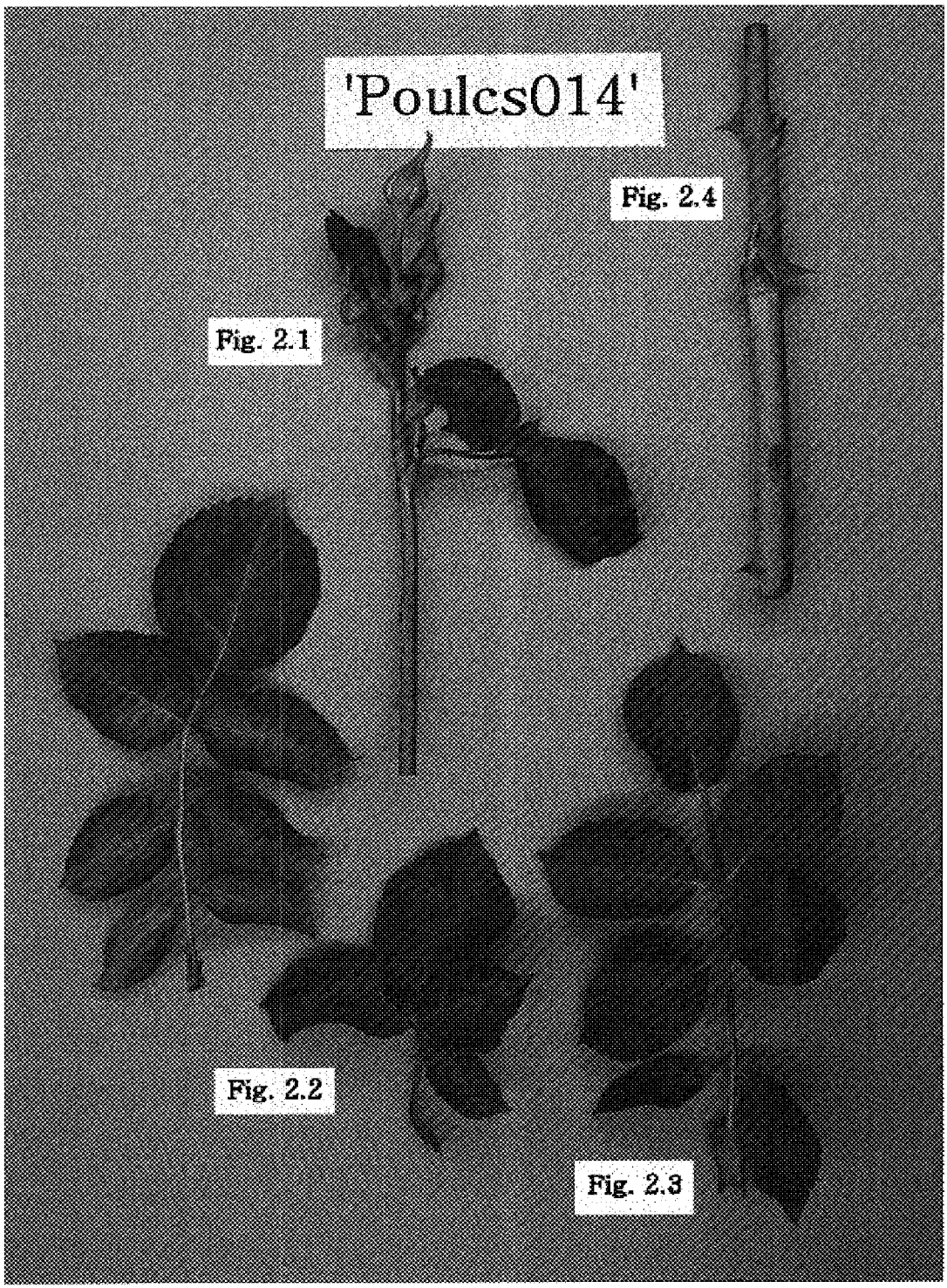
'Poulcs014'
Fig. 2.4
Fig. 2.1
Fig. 2.2
Fig. 2.3